(12) United States Patent
Sjong et al.

(10) Patent No.: US 9,945,982 B2
(45) Date of Patent: Apr. 17, 2018

(54) FLUORINATED SILOXANES AND METHODS FOR THEIR PREPARATION

(71) Applicant: EMPIRE TECHNOLOGY DEVELOPMENT LLC, Wilmington, DE (US)

(72) Inventors: Angele Sjong, Louisville, CO (US); Georgius Abidal Adam, Edensor Park (AU)

(73) Assignee: Empire Technology Development LLC, Wilmington, DE (US)

( * ) Notice: Subject to any disclaimer, the term of this patent is extended or adjusted under 35 U.S.C. 154(b) by 0 days.

(21) Appl. No.: 15/035,371

(22) PCT Filed: Nov. 8, 2013

(86) PCT No.: PCT/US2013/069088
§ 371 (c)(1),
(2) Date: May 9, 2016

(87) PCT Pub. No.: WO2015/069271
PCT Pub. Date: May 14, 2015

(65) Prior Publication Data
US 2016/0274272 A1    Sep. 22, 2016

(51) Int. Cl.
| | | |
|---|---|---|
| *C07F 7/00* | (2006.01) | |
| *G02B 1/04* | (2006.01) | |
| *C03C 25/10* | (2018.01) | |
| *C07F 7/21* | (2006.01) | |
| *C08F 130/08* | (2006.01) | |
| *C08G 77/24* | (2006.01) | |
| *G02B 6/10* | (2006.01) | |
| *C08G 77/04* | (2006.01) | |

(52) U.S. Cl.
CPC ............ *G02B 1/046* (2013.01); *C03C 25/104* (2013.01); *C07F 7/21* (2013.01); *C08F 130/08* (2013.01); *C08G 77/045* (2013.01); *C08G 77/24* (2013.01); *G02B 6/10* (2013.01)

(58) Field of Classification Search
CPC ........ C03C 25/104; C07F 7/21; C08F 130/08; C08G 77/045; G02B 6/10
USPC ....................................................... 556/443
See application file for complete search history.

(56) References Cited

U.S. PATENT DOCUMENTS

| | | |
|---|---|---|
| 2,905,703 A | 9/1959 | Bailey et al. |
| 3,221,040 A | 11/1965 | Peter |
| 3,433,765 A | 3/1969 | Geipel |
| 3,846,462 A | 11/1974 | Prokai et al. |
| 3,983,148 A | 9/1976 | Reedy et al. |
| 4,003,847 A | 1/1977 | Prokai |
| 4,317,616 A | 3/1982 | Clarke |
| 4,529,752 A | 7/1985 | Bluestein |
| 4,780,510 A | 10/1988 | Uemiya et al. |
| 4,877,528 A * | 10/1989 | Friesen .............. B01D 67/0093 210/500.29 |
| 2004/0076391 A1 | 4/2004 | Ghoshal et al. |
| 2008/0312365 A1* | 12/2008 | Maton .................... C08G 77/14 524/423 |
| 2012/0100474 A1 | 4/2012 | Hikosaka et al. |

FOREIGN PATENT DOCUMENTS

EP         0252665 A2    1/1988

OTHER PUBLICATIONS

Silicone Sponge and Silicone Rubber Gaskets, Seals, Cushions, and Materials, accessed at http://www.stockwell.com/data-sheets/silicone-materials-guide.pdf, accessed on Apr. 22, 2016, pp. 4.
Chang and Holguin, Electro-Optical Light Management Material: Low Refractive Index Pressure Sensitive Adhesives, The Journal of Adhesion (Jan. 25, 2007), 81(9) pp. 925-939.
Dubois et al., Spin-on Dielectric Materials, Dielectric Films for Advanced Microelectronics (2007), Chapter 2 pp. 33-83.
Grill, Low and Ultralow Dielectric Constant Films Prepared by Plasma-enhanced Chemical Vapor Deposition, Dielectric Films for Advanced Microelectronics (2007), Chapter 1 pp. 1-32.
International Search Report and Written Opinion for International Application No. PCT/US2013/069088 dated Jun. 5, 2014.
Liu et al., Synthesis of Crosslinkable Fluorinated Linear-Hyperbranched Copolyimides for Optical Waveguide Devices, Journal of Applied Polymer Science (May 9, 2012), 127(3) pp. 1834-1841.
Su et al., Siloxane materials for optical applications, Proceedings of SPIE Materials and Nanostructures (Jan. 23, 2006), (6029) pp. 60291C-1-60291C-8.

* cited by examiner

*Primary Examiner* — Sudhakar Katakam
*Assistant Examiner* — Kofi Adzamli
(74) *Attorney, Agent, or Firm* — Pepper Hamilton LLP

(57) ABSTRACT

Fluorinated siloxane compositions, and methods of making and using the fluorinated siloxanes are disclosed. The polymers described herein may exhibit self-healing properties, a low dielectric constant, and a low refractive index. In some embodiments, a method of making a siloxane compound may involve contacting a silicon metal with a fluorinated compound to form a dichlorosilane compound, hydrolyzing the dichlorosilane compound to form a fluorinated tetrasiloxane compound, and contacting the fluorinated tetrasiloxane compound with a metal catalyst to form a fluorinated cyclic siloxane (D4) compound.

28 Claims, No Drawings

FLUORINATED SILOXANES AND METHODS FOR THEIR PREPARATION

CROSS-REFERENCE TO RELATED APPLICATION

This Patent Application is a U.S. National Stage filing under 35 U.S.C. § 371 of International Patent Application No. PCT/US2013/069088, filed on Nov. 8, 2013 entitled "FLUORINATED SILOXANES AND METHODS FOR THEIR PREPARATION," which is incorporated herein by reference in its entirety.

BACKGROUND

The demand for a continuous increase in transmission speed, data capacity and data density in integrated optical and optoelectronic circuits has been the motivating force behind numerous innovations in areas of broadband communications, high-capacity information storage, and large screen and portable information display. Although glass optical fibers are routinely used for high-speed data transfer over long distances, they are inconvenient for complex high-density circuitry because of their high density, poor durability and high cost of fabrication for complex photonic circuits. Thus, there is a need to develop alternative materials that can at least ameliorate or address the aforementioned problems. Such materials can be envisioned to be stable during phase transitions (for example, crystallization or melting), chemically stable, and stable in terms of optical loss, index of refraction, and density.

SUMMARY

This disclosure is related to compositions of fluorinated siloxanes, and methods of making and their use. In an embodiment, a compound is of formula I:

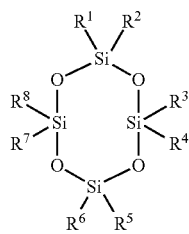

(I)

wherein each $R^1$, $R^2$, $R^3$, $R^4$, $R^5$, $R^6$, $R^7$, and $R^8$ is, independently, $-CF_3$, $-CF_2-$, $-CF_2H$, $-CF_2-C(=O)-F$, $-C_6F_5$, $-CF=CF_2$, $-CF_2-CF=CF_2$, or

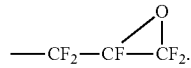

In an additional embodiment, a compound is of formula II:

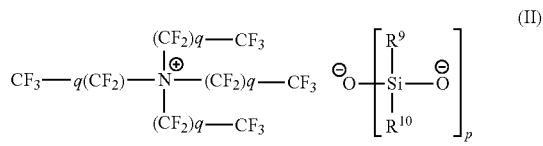

(II)

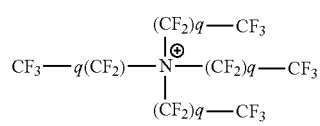

wherein each $R^9$ is, independently, $-CF_3$, $-CF_2-C(=O)-F$, $-C_6F_5$, $-CF=CF_2$, $-CF_2-CF=CF_2$, or

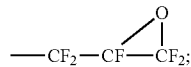

each $R^{10}$ is, independently, $-CF_3$, $-CF_2-C(=O)-F$, $-C_6F_5$, $-CF=CF_2$, $-CF_2-CF=CF_2$, or

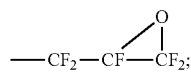

p is 1 or 2; and q is 1 or 2.

In a further embodiment, a compound is of formula III:

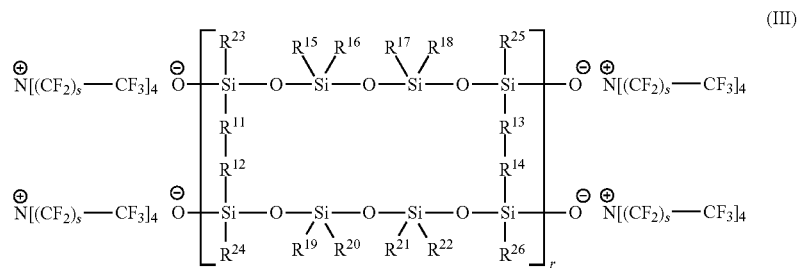

(III)

wherein r is an integer from 1 to 100; s is an integer from 1 to 3; $R^{11}$, $R^{12}$, $R^{13}$, and $R^{14}$ are each —$CF_2$—; and each $R^{15}$, $R^{16}$, $R^{17}$, $R^{18}$, $R^{19}$, $R^{20}$, $R^{21}$, $R^{22}$, $R^{23}$, $R^{24}$, $R^{25}$, and $R^{26}$ independently are, —$CF_3$, —$CF_2$—C(=O)—F, —$C_6F_5$, —CF=$CF_2$, —$CF_2$—CF=$CF_2$,

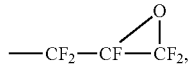

or salts thereof.

In an additional embodiment, an article or a polymer may include one or more compounds of formula I, II or III as described herein. In another embodiment, an optical waveguide structure may include a light transmitting core material having a first refractive index, and a cladding material contacting partially or entirely surrounding the core material, wherein the cladding material has a second refractive index lower than the first refractive index of the core material, and wherein the core material may include one or more compounds of formulae I, II, or III as described herein.

In a further embodiment, a method of making a siloxane compound of formula I may involve contacting a silicon metal with a fluorinated compound to form a dichlorosilane compound, hydrolyzing the dichlorosilane compound to form a fluorinated tetrasiloxane compound with hydroxyl groups, and contacting the fluorinated tetrasiloxane compound with hydroxyl groups with a metal catalyst to form a fluorinated cyclic siloxane (D4) compound.

In yet another embodiment, a method of making a compound of formula II may involve contacting a silicon metal with a fluorinated compound to form a dichlorosilane compound, hydrolyzing the dichlorosilane compound to form a fluorinated tetrasiloxane compound, contacting the fluorinated tetrasiloxane compound with a metal catalyst to form a fluorinated cyclic siloxane (D4) monomer, and contacting the fluorinated cyclic siloxane (D4) monomer with fluorinated tetramethyl-ammonium chloride.

DETAILED DESCRIPTION

This disclosure is not limited to the particular systems, devices and methods described, as these may vary. The terminology used in the description is for the purpose of describing the particular versions or embodiments only, and is not intended to limit the scope.

A "core material" refers to any layer of an optical waveguide that transmits light. A "cladding material" refers to any layer of an optical waveguide that confines light. In an embodiment, a core layer may be at least partially encompassed by a cladding layer.

A "waveguide" refers to a system having a material that provides a path to guide an electromagnetic wave. A waveguide may have, for example and without limitation, a circular or a rectangular shape.

In some embodiments, a compound is of formula I:

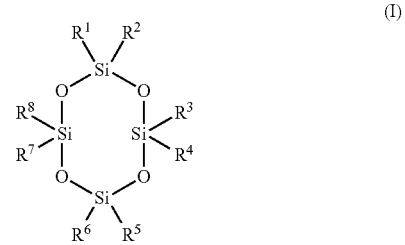

wherein each $R^1$ may be, independently, —$CF_3$, —$CF_2$—, —$CF_2H$, —$CF_2$—C(=O)—F, —$C_6F_5$, —CF=$CF_2$, —$CF_2$—CF=$CF_2$, or

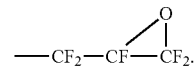

In some embodiments, each $R^1$ may be, independently, —$CF_3$, —$CF_2H$, or —$CF_2$—C(=O)—F.

In some embodiments, each $R^2$ may be, independently, —$CF_3$, —$CF_2$—, —$CF_2H$, —$CF_2$—C(=O)—F, —$C_6F_5$, —CF=$CF_2$, —$CF_2$—CF=$CF_2$, or

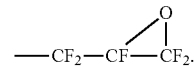

In some embodiments, each $R^2$ may be, independently, —$CF_3$, —$CF_2H$, or —$CF_2$—C(=O)—F.

In some embodiments, each $R^3$ may be, independently, —$CF_3$, —$CF_2$—, —$CF_2H$, —$CF_2$—C(=O)—F, —$C_6F_5$, —CF=$CF_2$, —$CF_2$—CF=$CF_2$, or

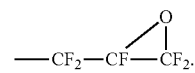

In some embodiments, each $R^3$ may be, independently, —$CF_3$, —$CF_2H$, or —$CF_2$—C(=O)—F.

In some embodiments, each $R^4$ may be, independently, —$CF_3$, —$CF_2$—, —$CF_2H$, —$CF_2$—C(=O)—F, —$C_6F_5$, —CF=$CF_2$, —$CF_2$—CF=$CF_2$, or

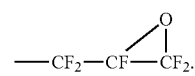

In some embodiments, each $R^4$ may be, independently, —$CF_3$, —$CF_2H$, or —$CF_2$—C(=O)—F.

In some embodiments, each $R^5$ may be, independently, —$CF_3$, —$CF_2$—, —$CF_2H$, —$CF_2$—C(=O)—F, —$C_6F_5$, —CF=$CF_2$, —$CF_2$—CF=$CF_2$, or

In some embodiments, each $R^5$ may be, independently, —$CF_3$, —$CF_2H$, or —$CF_2$—$C(=O)$—F.

In some embodiments, each $R^6$ may be, independently, —$CF_3$, —$CF_2$—, —$CF_2H$, —$CF_2$—$C(=O)$—F, —$C_6F_5$, —$CF=CF_2$, —$CF_2$—$CF=CF_2$, or

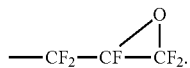

In some embodiments, each $R^6$ may be, independently, —$CF_3$, —$CF_2H$, or —$CF_2$—$C(=O)$—F.

In some embodiments, each $R^7$ may be, independently, —$CF_3$, —$CF_2$—, —$CF_2H$, —$CF_2$—$C(=O)$—F, —$C_6F_5$, —$CF=CF_2$, —$CF_2$—$CF=CF_2$, or

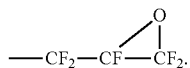

In some embodiments, each $R^7$ may be, independently, —$CF_3$, —$CF_2H$, or —$CF_2$—$C(=O)$—F.

In some embodiments, each $R^8$ may be, independently, —$CF_3$, —$CF_2$—, —$CF_2H$, —$CF_2$—$C(=O)$—F, —$C_6F_5$, —$CF=CF_2$, —$CF_2$—$CF=CF_2$, or

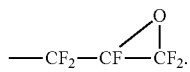

In some embodiments, each $R^8$ may be, independently, —$CF_3$, —$CF_2H$, or —$CF_2$—$C(=O)$—F.

Non-limiting examples of compounds represented by formula I include, but are not limited to, the following compounds:

1

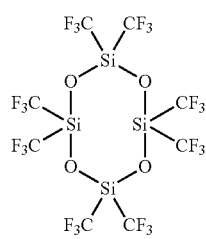

2

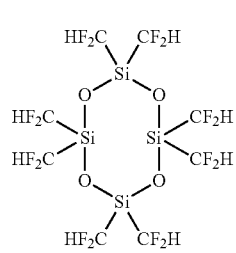

-continued

3

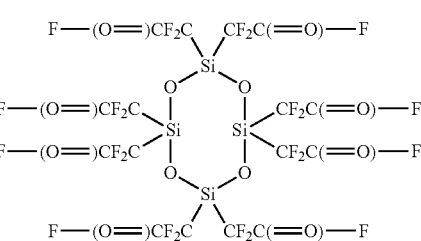

4

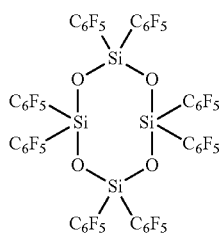

5

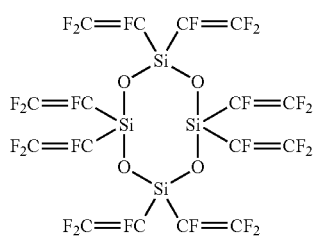

6

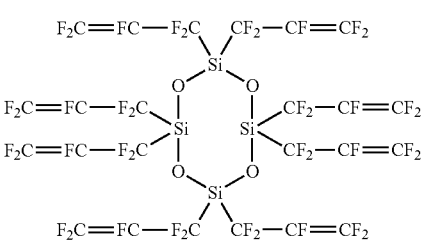

7

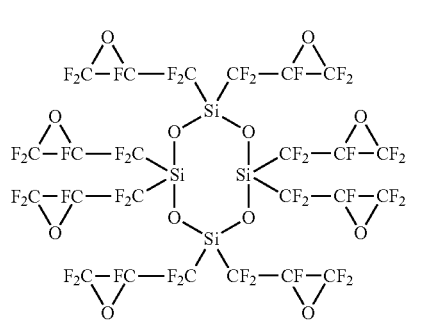

In some embodiments, a compound is of formula II:

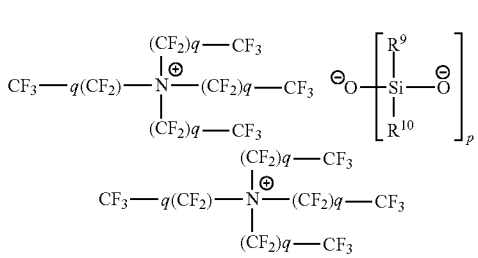

(II)

wherein each $R^9$ may be, independently, $-CF_3$, $-CF_2-C(=O)-F$, $-C_6F_5$, $-CF=CF_2$, $-CF_2-CF=CF_2$, or

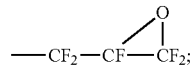

each $R^{10}$ may be, independently, $CF_3$, $-CF_2-C(=O)-F$, $-C_6F_5$, $-CF=CF_2$, $-CF_2-CF=CF_2$, or

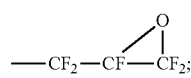

p is 1 or 2; and q is 1 or 2.

In some embodiments, each $R^9$ may be, independently, $-CF_3$; each $R^{10}$ may be, independently, $CF_3$; p is 2; and q is 1.

In some embodiments, each $R^9$ is

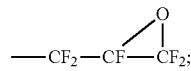

each $R^{10}$ is

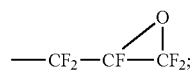

p is 2; and q is 1.

In some embodiments, each $R^9$ is $-CF_2-C(=O)-F$; each $R^{10}$ is $-CF_2-C(=O)-F$; p is 2; and q is 1.

In some embodiments, each $R^9$ is $-C_6F_5$; each $R^{10}$ is $-C_6F_5$; p is 2; and q is 1.

In some embodiments, each $R^9$ is $-CF=CF_2$; each $R^{10}$ is $-CF=CF_2$; p is 2; and q is 1. The compounds of formula II may function as an anionic catalyst during polymerization.

Non-limiting examples of compounds represented by formula II include, but are not limited to, the following compounds:

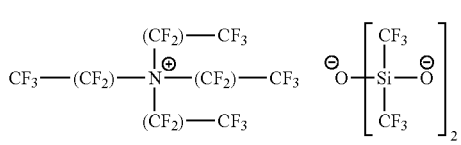

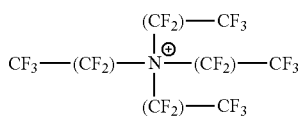

In some embodiments, a compound is of formula III:

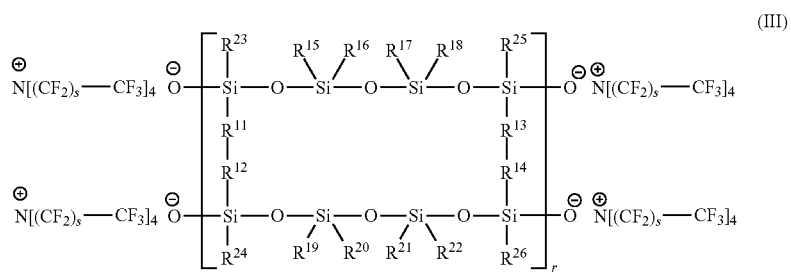

wherein r may be an integer from 1 to 100; s may be an integer from 1 to 3; $R^{11}$, $R^{12}$, $R^{13}$, and $R^{14}$ are each —$CF_2$—; and each $R^{15}$, $R^{16}$, $R^{17}$, $R^{18}$, $R^{19}$, $R^{20}$, $R^{21}$, $R^{22}$, $R^{23}$, $R^{24}$, $R^{25}$, and $R^{26}$ independently may be, —$CF_3$, —$CF_2$—C(=O)—F, —$C_6F_5$, —CF=$CF_2$, —$CF_2$—CF=$CF_2$,

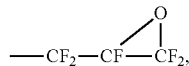

or salts thereof. In some embodiments, each of $R^{15}$, $R^{16}$, $R^{17}R^{18}$, $R^{19}$, $R^{20}$, $R^{21}$, $R^{22}$, $R^{23}$, $R^{24}$, $R^{25}$, and $R^{26}$ independently may be, —$CF_3$, —$CF_2$—C(=O)—F, —$C_6F_5$, or —CF=$CF_2$.

Non-limiting examples of compounds represented by formula III include, but are not limited to, the following compounds:

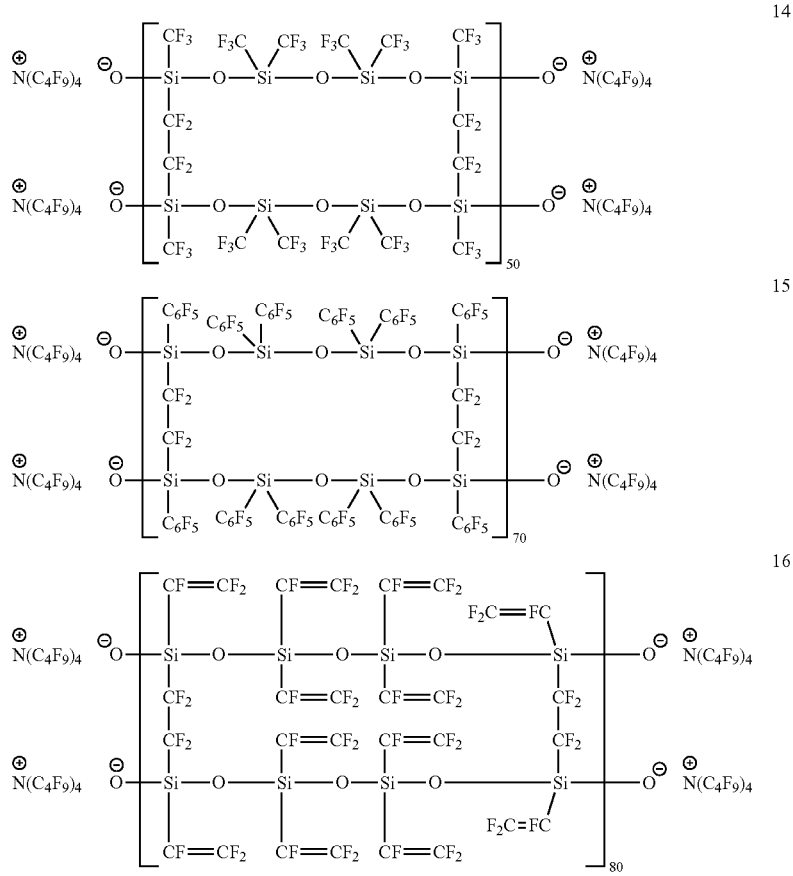

Compounds of formula III may be considered to be a "living polymer network" because the tetrafluoroalkyl ammonium end groups may react with the network chains to restructure the crosslinks in the network. For example, when the polymer is subjected to temperatures above 300° C., the polymer active chain ends are transferred to Si—O—$C_4F_9$, and the catalyst is transferred to $N(C_4F_9)_3$ and siloxane oligomer, which is available at any time for further polymerization. While self-alignment occurs at such high temperatures via anionic polymerization, neither thermal degradation nor melting occurs. The presence of fluorine substituent groups in the catalyst and siloxane backbone increases the anionic initiation activity of both the catalyst and the monomer due to the high electronegativity and electron withdrawing properties.

In some embodiments, a method of making a compound of formula I may involve contacting a silicon metal with a fluorinated compound to form a dichlorosilane compound, hydrolyzing the dichlorosilane compound to form a fluorinated tetrasiloxane compound with hydroxyl groups, and contacting the fluorinated tetrasiloxane compound with hydroxyl groups with a metal catalyst to form a fluorinated cyclic siloxane (D4) compound of formula I. Examples of fluorinated compounds that may be used are trifluorochloromethane, difluorochloromethane, fluorinated phenyldiazonium chloride, fluorinated vinylchloride, fluorinated allylchloride, and fluorinated epichlorohydrin. The dichlorosilane compound may be subjected to a controlled hydrolysis step to form fluorinated tetrasiloxane compounds. The hydroxyl terminated tetrasiloxane compound may undergo cyclization in the presence of zinc oxide to form a fluorinated cyclic siloxane (D4) compound. Other metal catalysts that may be used are oxides of Li, K, Ba, Ca, Na, Mg, Al, Mn, Zn, Cr, and any combination thereof.

In some embodiments, the cyclic siloxane (D4) monomer obtained by the methods described herein may be polymerized using a cationic catalyst, such as trifluoromethanesulphonic acid. This polymerization would cause breakage of Si—O bonds, resulting in ring opening to form polymers. The polymer may be represented by the structure below:

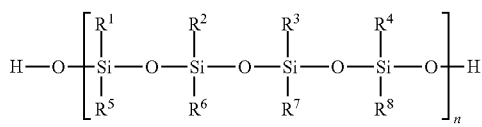

IV

In other embodiments, the cyclic siloxane (D4) monomer units may be coupled together in the presence of fluorinated benzoyl peroxide to form polymers. Examples of such polymers include compounds 8 and 9, as shown below:

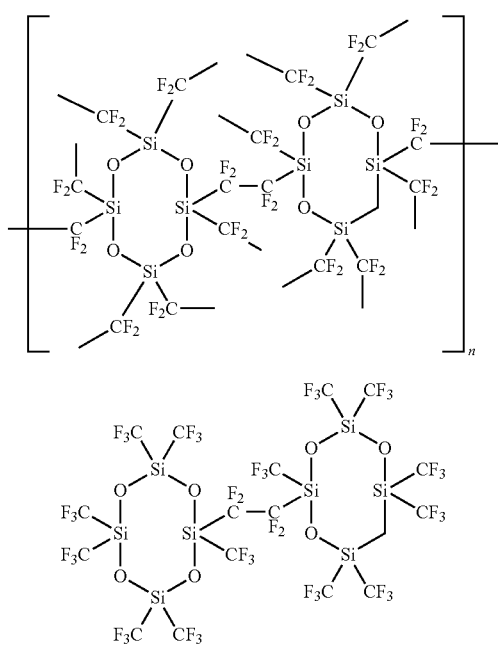

In some embodiments, a method of preparing the compound of formula II may involve contacting a silicon metal with a fluorinated compound to form a dichlorosilane compound, hydrolyzing the dichlorosilane compound to form a fluorinated tetrasiloxane compound, contacting the fluorinated tetrasiloxane compound with a metal catalyst to form a fluorinated cyclic siloxane (D4) monomer, and contacting the fluorinated cyclic siloxane (D4) monomer with fluorinated tetramethyl-ammonium chloride. During contacting the fluorinated cyclic siloxane (D4) monomer with fluorinated tetramethylammonium chloride, the reaction temperature may be below 10° C., below 8° C., below 6° C., below 4° C. or below 0° C.

The compounds and polymers disclosed herein may have high thermal stability, good mechanical properties, self-healing properties, a low dielectric constant, and a low refractive index. Due to their high thermal stability, thermal degradation may not occur during high temperature processing, for example, a solder reflow process in the manufacturing of optical circuits. Since the compounds and polymers are prepared by anionic living polymerization, they maintain the active catalyst, active polymerizable chain end and cyclic structure in the system thereby meeting the fundamental requirements of being printable waveguide materials. Such compounds and polymers may be used in optical waveguides, tires, mechanical parts of a vehicle, sporting goods, coupling sockets, switches, printed wiring board pins, ice skating rinks, and the like.

The compounds and polymers disclosed herein may be used for preparing optical waveguides. An optical waveguide structure may have a light transmitting core material having a first refractive index, and a cladding material partially contacting or entirely surrounding the core material, wherein the cladding material has a second refractive index lower than the first refractive index of the core material, and wherein the core material includes one or more compounds of formula I, II or III.

The optical waveguides may be synthesized using any method known in the art. Briefly, a layer of cladding material is formed over a suitable substrate. The substrate may be any material upon which it is desired to establish a waveguide, such as a semiconductor material (silicon, silicon oxide, silicon oxide/silicon, gallium arsenide, silicon nitride, silica on silicon, or the like), glass, plastics, quartz, ceramics, or crystalline materials. The cladding material may be formed on the substrate by any known method, such as spin casting, dip coating, roller coating, doctor blading, or evaporating. Suitable cladding materials include silica xerogels, silicon oxide, metal oxides, air, silicon dioxide, benzocyclobutene, plasma oxides, acrylates, fluorinated acrylates, polyimides, and other polymers having a lower refractive index than the core. The siloxane core material can then be deposited into a thin film on top of the cladding. Before or after curing, the core siloxane material can optionally be patterned using known methods, such as photolithography, wet etching, reactive-ion etching (RIE), photoablation, and the like.

EXAMPLES

Example 1

Preparation of Compound 1 and its Polymer

About 0.1 mole of silicon metal is reacted with about 0.2 moles of trifluorochloromethane to obtain hexafluorodimethyl dichlorosilane. The hexafluorodimethyl dichlorosilane is subjected to controlled hydrolysis to obtain a hydroxyl terminated fluorinated tetrasiloxane compound. The tetrasiloxane compound undergoes cyclization in the presence of zinc oxide to obtain a fluorinated cyclic siloxane (D4) compound 1.

About 20 grams of the compound 1 obtained above is charged into a reaction vessel along with 20 µL of the cationic catalyst trifluoromethanesulphonic acid (triflic acid). The reaction mixture is maintained at 10° C. under inert conditions, and mixed for 8-12 hours. At the end of the reaction, the polymer is separated and dissolved in chloroform, re-precipitated with methanol, and dried under vacuum to obtain a polymer of compound 1.

Example 2

Preparation of Compound 4 and its Polymer

About 0.1 mole of silicon metal is reacted with about 0.2 moles of fluorinated phenyldiazonium chloride to obtain a fluorinated diphenyl dichlorosilane compound. The fluorinated diphenyl dichlorosilane compound is subjected to controlled hydrolysis to obtain a fluorinated tetrasiloxane compound. The tetrasiloxane compound undergoes cyclization in the presence of zinc oxide to obtain a fluorinated cyclic siloxane (D4) compound 4.

About 20 grams of the compound 4 obtained above is charged into a reaction vessel along with 20 µL of the cationic catalyst trifluoromethanesulphonic acid (triflic acid). The reaction mixture is maintained at 10° C. under inert conditions, and mixed for 8-12 hours. At the end of the reaction, the polymer is separated and dissolved in chloroform, re-precipitated with methanol, and dried under vacuum to obtain a polymer of compound 4.

Example 3

Preparation of Compound 5 and its Polymer

About 0.1 mole of silicon metal is reacted with about 0.2 moles of fluorinated vinylchloride to obtain a fluorinated divinyl dichlorosilane compound. The fluorinated divinyl dichlorosilane compound is subjected to controlled hydrolysis to obtain a fluorinated tetrasiloxane compound. The tetrasiloxane compound undergoes cyclization in the presence of zinc oxide to obtain a fluorinated cyclic siloxane (D4) compound 5.

About 20 grams of the compound 5 obtained above is charged into a reaction vessel along with 20 µL of the cationic catalyst trifluoromethanesulphonic acid (triflic acid). The reaction mixture is maintained at 10° C. under inert conditions, and mixed for 8-12 hours. At the end of the reaction, the polymer is separated and dissolved in chloroform, re-precipitated with methanol, and dried under vacuum to obtain a polymer of compound 5.

Example 4

Preparation of Compound 6 and its Polymer

About 0.1 mole of silicon metal is reacted with about 0.2 moles of fluorinated allylchloride to obtain a fluorinated diallyl dichlorosilane compound. The fluorinated diallyl dichlorosilane compound is subjected to controlled hydrolysis to obtain a fluorinated tetrasiloxane compound. The tetrasiloxane compound undergoes cyclization in the presence of zinc oxide to obtain a fluorinated cyclic siloxane (D4) compound 6.

About 20 grams of the compound 6 obtained above is charged into a reaction vessel along with 20 µL of the cationic catalyst trifluoromethanesulphonic acid (triflic acid). The reaction mixture is maintained at 10° C. under inert conditions, and mixed for 8-12 hours. At the end of the reaction, the polymer is separated and dissolved in chloroform, re-precipitated with methanol, and dried under vacuum to obtain a polymer of compound 6.

Example 5

Preparation of Compound 7 and its Polymer

About 0.1 mole of silicon metal is reacted with about 0.2 moles of fluorinated epichlorohydrin to obtain a fluorinated bis-glycidylether dichlorosilane compound. The fluorinated bis-glycidylether dichlorosilane compound is subjected to controlled hydrolysis to obtain a fluorinated tetrasiloxane compound. The tetrasiloxane compound undergoes cyclization in the presence of zinc oxide to obtain a fluorinated cyclic siloxane (D4) compound 7.

About 20 grams of the compound 7 obtained above is charged into a reaction vessel along with 20 µL of the cationic catalyst trifluoromethanesulphonic acid (triflic acid). The reaction mixture is maintained at 10° C. under inert conditions, and mixed for 8-12 hours. At the end of the reaction, the polymer is separated and dissolved in chloroform, re-precipitated with methanol, and dried under vacuum to obtain a polymer of compound 7.

Example 6

Preparation of Compound 8

About 0.1 mole of silicon metal is reacted with about 0.2 moles of difluorochloromethane to obtain bis(difluoromethyl) dichlorosilane. The bis(difluoromethyl) dichlorosilane is subjected to controlled hydrolysis to obtain a fluorinated tetrasiloxane compound. The tetrasiloxane compound undergoes cyclization in the presence of zinc oxide to obtain a fluorinated cyclic siloxane (D4) monomer.

About 10 grams of the fluorinated cyclic siloxane (D4) monomer is mixed with 0.001 gram of fluorinated benzoyl peroxide and heated in a mold under $N_2$ atmosphere at 120° C. A coupling reaction takes place resulting in a polymeric compound 8, having fluorinated ethylene linkages between the siloxane units.

Example 7

Preparation of Compound 9

About 3 moles of hexafluorodimethyl dichlorosilane and 2 moles of trifluoromethyl-difluoromethyl dichlorosilane are mixed and subjected to controlled hydrolysis to obtain a fluorinated tetrasiloxane compound. The tetrasiloxane compound undergoes cyclization in the presence of zinc oxide to obtain a fluorinated cyclic siloxane (D4) monomer.

About 20 grams of the cyclic siloxane (D4) monomer is mixed with 0.001 grams of the fully fluorinated benzoyl peroxide and heated at 120° C. for 30 minutes. The free radical coupling reaction takes place forming compound 9 which can be used as a laddering agent and as ring opening polymerisation monomer Example 8

Preparation of Anionic Catalyst Compound 10

The reaction vessel is charged with 0.1 mole of fully fluorinated tetrabutyl- ammonium chloride that is prepared by reacting fluorinated tributylamine with fluorinated butyl chloride. The reaction vessel is cooled to 5° C., flushed with $N_2$, and about 0.05 mole of the fluorinated cyclic siloxane (D4) monomer of Example 1 is added. The reaction is continued for one hour under $N_2$ atmosphere, and the product is purified and dried to obtain an anionic catalyst compound 10.

Example 9

Preparation of Compound 14

About 1 mole of compound 1 is mixed with 0.1 mole of compound 9 in the presence of the anionic catalyst compound 10. The mixture is cooled to 0° C. for 40 minutes under a stream of nitrogen gas. The resulting polymer is a ladder type anionic living polysiloxane polymer compound 14. The degree of laddering can be controlled by the molar ratio of compound 1 and compound 9. The reaction can be carried out in aprotic solvents. The polymer that is formed can be considered as a "living polymer network" as the active polymerizable chain end groups can react with the network chains to restructure the crosslinks in the network, giving the polymer its self-aligning property. In addition, the polymer may have high thermal stability, good mechanical properties, self-healing properties, a low dielectric constant, and a low refractive index.

Example 10

Preparation of a Waveguide

Planar waveguides are made on 3 inch (7.62 cm) silicon wafer substrates using the siloxane polymers of compounds 4-7 as the high refractive index core material, and silicon oxide as the cladding. The silicon oxide is spin-coated on a wafer to a thickness of about 1 pm. The core material (compounds 4-7) is then spun-onto the cladding film to a thickness of about 2 μm (6000 rpm for 100 seconds). Next, the samples are baked at 100° C. for 20 minutes and annealed at 150° C. As the siloxane polymers are expected to have high thermal stability, thermal degradation may not occur during subsequent high temperature processing, for example, a solder reflow process in the manufacturing of optical circuits containing the planar waveguides. The waveguide may also have good mechanical properties, self-healing properties, a low dielectric constant, and a low refractive index.

Example 11

An Article Prepared from Siloxane Polymers

The siloxane polymer pellets of compound 1 are heated in an injection molding machine and fed into a mold cavity and allowed to cool. The cooled polymer obtains the shape according to the contour of the cavity, and articles such as coupling sockets, switches, tennis rackets, and brake pads may be manufactured using appropriate molds. It will be expected that the articles manufactured from the siloxane polymer may have high thermal stability, good mechanical properties, self-healing properties, a low dielectric constant, and a low refractive index.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases at least one and one or more to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases one or more or "at" least one and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

What is claimed is:

1. A compound of formula I:

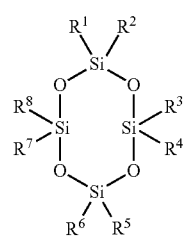

(I)

wherein
each of $R^1$, $R^2$, $R^3$, $R^4$, $R^5$, $R^6$, $R^7$, and $R^8$ is, independently, —$CF_2H$, —$CF_2$—C(=O)—F, —$C_6F_5$, —CF=$CF_2$, —$CF_2$—CF=$CF_2$, or

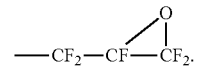

2. The compound of claim 1, wherein $R^1$ is, one of, —$CF_2H$ or —$CF_2$—C(=O)—F.
3. The compound of claim 1, wherein $R^2$ is, one of, —$CF_2H$ or —$CF_2$—C(=O)—F.
4. The compound of claim 1, wherein $R^3$ is, one of, —$CF_2H$ or —$CF_2$—C(=O)—F.
5. The compound of claim 1, wherein $R^4$ is, one of, —$CF_2H$ or —$CF_2$—C(=O)—F.
6. The compound of claim 1, wherein $R^5$ is, one of, —$CF_2H$ or —$CF_2$—C(=O)—F.
7. The compound of claim 1, wherein $R^6$ is, one of, —$CF_2H$ or —$CF_2$—C(=O)—F.
8. The compound of claim 1, wherein $R^7$ is, one of, —$CF_2H$ or —$CF_2$—C(=O)—F.
9. The compound of claim 1, wherein $R^8$ is, one of, —$CF_2H$ or —$CF_2$—C(=O)—F.
10. The compound of claim 1, wherein: each of $R^1$, $R^2$, $R^3$, $R^4$, $R^5$, $R^6$, $R^7$, and $R^8$ is, independently, —$CF_2H$.
11. The compound of claim 1, wherein each of $R^1$, $R^2$, $R^3$, $R^4$, $R^5$, $R^6$, $R^7$, and $R^8$ is, independently, —$CF_2$—C(=O)—F.
12. The compound of claim 1, wherein each of $R^1$, $R^2$, $R^3$, $R^4$, $R^5$, $R^6$, $R^7$, and $R^8$ is, independently, —$C_6F_5$.
13. The compound of claim 1, wherein each of $R^1$, $R^2$, $R^3$, $R^4$, $R^5$, $R^6$, $R^7$, and $R^8$ is, independently, —CF=$CF_2$.
14. The compound of claim 1, wherein each of $R^1$, $R^2$, $R^3$, $R^4$, $R^5$, $R^6$, $R^7$, and $R^8$ is, independently, —$CF_2$—CF=$CF_2$.
15. The compound of claim 1, wherein each of $R^1$, $R^2$, $R^3$, $R^4$, $R^5$, $R^6$, $R^7$, and $R^8$ is, independently,

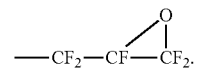

16. An optical waveguide structure comprising:
a light transmitting core material having a first refractive index; and
a cladding material partially contacting or entirely surrounding the light transmitting core material, wherein the cladding material has a second refractive index lower than the first refractive index of the light transmitting core material, and wherein the light transmitting core material comprises one or more compounds according to formula I:

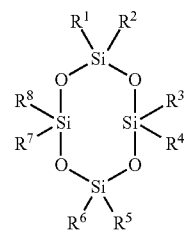

(I)

wherein each of $R^1$, $R^2$, $R^3$, $R^4$, $R^5$, $R^6$, $R^7$, and $R^8$ is, independently, —$CF_2H$, —$CF_2$—C(=O)—F, —$C_6F_5$, —CF=$CF_2$, —$CF_2$—CF=$CF_2$, or

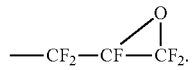

17. A method of making a siloxane compound of formula I:

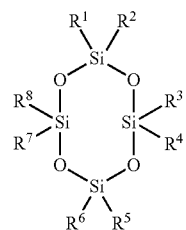 (I)

wherein each of $R^1$, $R^2$, $R^3$, $R^4$, $R^5$, $R^6$, $R^7$, and $R^8$ is, independently, —$CF_2H$, —$CF_2$—C(=O)—F, —$C_6F_5$, —CF=$CF_2$, —$CF_2$—CF=$CF_2$, or

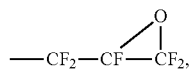

the method comprising:
- contacting a silicon metal with a fluorinated compound to form a dichlorosilane compound;
- hydrolyzing the dichlorosilane compound to form a fluorinated tetrasiloxane compound with hydroxyl groups; and
- contacting the fluorinated tetrasiloxane compound with hydroxyl groups with a metal catalyst to form a fluorinated cyclic siloxane (D4) compound of formula I.

18. The method of claim 17, wherein contacting the silicon metal comprises contacting with trifluorochloromethane, difluorochloromethane, fluorinated phenyldiazonium chloride, fluorinated vinylchloride, fluorinated allylchloride, fluorinated epichlorohydrin, or any combination thereof.

19. The method of claim 17, wherein hydrolyzing the dichlorosilane compound comprises controlled hydrolysis of the dichlorosilane compound.

20. The method of claim 17, wherein contacting the fluorinated tetrasiloxane compound comprises contacting with oxides of Li, K, Ba, Ca, Na, Mg, Al, Mn, Zn, Cr, or any combination thereof.

21. The optical waveguide structure of claim 16, wherein the light transmitting core material comprises the compound of formula I, wherein each of $R^1$, $R^2$, $R^3$, $R^4$, $R^5$, $R^6$, $R^7$, and $R^8$ is, independently, —$CF_2H$, or —$CF_2$—C(=O)—F.

22. The optical waveguide structure of claim 16, wherein the light transmitting core material comprises the compound of formula I, wherein each of $R^1$, $R^2$, $R^3$, $R^4$, $R^5$, $R^6$, $R^7$, and $R^8$ is, independently —$CF_2H$.

23. The optical waveguide structure of claim 16, wherein the light transmitting core material comprises the compound of formula I, wherein each of $R^1$, $R^2$, $R^3$, $R^4$, $R^5$, $R^6$, $R^7$, and $R^8$ is, independently, —$CF_2H$.

24. The optical waveguide structure of claim 16, wherein the light transmitting core material comprises the compound of formula I, wherein each of $R^1$, $R^2$, $R^3$, $R^4$, $R^5$, $R^6$, $R^7$, and $R^8$ is, independently, —$CF_2$—C(=O)—F.

25. The optical waveguide structure of claim 16, wherein the light transmitting core material comprises the compound of formula I, wherein each of $R^1$, $R^2$, $R^3$, $R^4$, $R^5$, $R^6$, $R^7$, and $R^8$ is, independently, —$C_6F_5$.

26. The optical waveguide structure of claim 16, wherein the light transmitting core material comprises the compound of formula I, wherein each of $R^1$, $R^2$, $R^3$, $R^4$, $R^5$, $R^6$, $R^7$, and $R^8$ is, independently, —CF=$CF_2$.

27. The optical waveguide structure of claim 16, wherein the light transmitting core material comprises the compound of formula I, wherein each of $R^1$, $R^2$, $R^3$, $R^4$, $R^5$, $R^6$, $R^7$, and $R^8$ is, independently, —$CF_2$—CF=$CF_2$.

28. The optical waveguide structure of claim 16, wherein the light transmitting core material comprises the compound of formula I, wherein each of $R^1$, $R^2$, $R^3$, $R^4$, $R^5$, $R^6$, $R^7$, and $R^8$ is, independently,

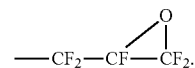

* * * * *